(12) United States Patent
Bokel et al.

(10) Patent No.: US 6,646,136 B1
(45) Date of Patent: Nov. 11, 2003

(54) CHROMAN DERIVATIVES

(75) Inventors: Heinz-Herman Bokel, Darmstadt (DE); Peter Mackert, Egelsbach (DE); Christoph Müramann, Reinheim (DE); Nobert Schweickert, Seeheim-Jugenheim (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 09/868,704
(22) PCT Filed: Dec. 1, 1999
(86) PCT No.: PCT/EP99/09333
§ 371 (c)(1), (2), (4) Date: Feb. 28, 2002
(87) PCT Pub. No.: WO00/35901
PCT Pub. Date: Jun. 22, 2000

(30) Foreign Application Priority Data

Dec. 17, 1998 (DE) .......................... 198 58 341

(51) Int. Cl.[7] .............................................. C07D 311/76
(52) U.S. Cl. ....................................... 549/399; 549/407
(58) Field of Search .................................. 549/407, 399

(56) References Cited

U.S. PATENT DOCUMENTS 5,962,513 A * 10/1999 Schohe-Loop et al. ..... 524/456

FOREIGN PATENT DOCUMENTS

EP 0 540 914 A 5/1993
EP 0 707 007 A 4/1996

* cited by examiner

Primary Examiner—Alan L. Rotman
Assistant Examiner—Raymond Covington
(74) Attorney, Agent, or Firm—Millen, White, Zelano & Branigan, P.C.

(57) ABSTRACT

Chroman derivatives of the formula I

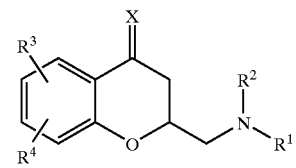

in which $R^1$ is acyl having 1–6 C atoms, —CO—$R^5$ or an amino protective group, $R^2$ is H or alkyl having 1–6 C atoms, $R^3$, $R^4$ in each case independently of one another are H, alkyl having 1–6 C atoms, CN, Hal or $COOR^2$, $R^5$ is phenyl which is unsubstituted or mono- or disubstituted by alkyl having 1–6 C atoms, $OR^2$ or Hal, X is H, H or O, Hal is F, Cl, Br or I, and their salts, are suitable as intermediates in the synthesis of medicaments.

28 Claims, No Drawings

CHROMAN DERIVATIVES

This application is a 371 of PCT/EP99/09333 filed Dec. 1, 1999.

The invention relates to chroman derivatives of the formula I

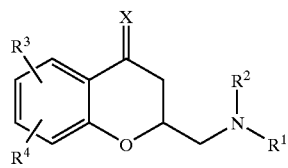

in which
- R$^1$ is acyl having 1–6 C atoms, —CO—R$^5$ or an amino protective group,
- R$^2$ is H or alkyl having 1–6 C atoms,
- R$^3$, R$^4$ in each case independently of one another are H, alkyl having 1–6 C atoms, CN, Hal or COOR$^2$.
- R$^5$ is phenyl which is unsubstituted or mono- or disubstituted by alkyl having 1–6 C atoms, OR$^2$ or Hal,
- X is H,H or O,
- Hal is F, Cl, Br or I, and their salts.

The invention also relates to the optically active forms, the racemates, the enantiomers and also the hydrates and solvates, e.g. alcoholates, of these compounds.

Similar compounds are disclosed in EP 0 707 007.

The invention was based on the object of finding novel compounds which can be used, in particular, as intermediates in the synthesis of medicaments.

It has been found that the compounds of the formula I and their salts are important intermediates for the preparation of medicaments, in particular of those which show, for example, actions on the central nervous system.

The invention relates to the chroman derivatives of the formula I and their salts.

Above and below, the radicals R$^1$, R$^2$, R$^3$, R$^4$, R$^5$ and X have the meanings indicated in the formulae I and II, if not expressly stated otherwise.

In the above formulae, alkyl has 1 to 6, preferably 1, 2, 3 or 4, C atoms. Alkyl is preferably methyl or ethyl, furthermore propyl, isopropyl, in addition also butyl, isobutyl, sec-butyl or tert-butyl. Acyl has 1 to 6, preferably 1, 2, 3 or 4, C atoms Acyl is in particular acetyl, propionyl or butyryl.

R$^2$ is preferably H, in addition also methyl, ethyl or is propyl.

R$^3$ and R$^1$ are preferably H.

R$^5$ is preferably, for example, phenyl, o-, m- or p-tolyl, o-, m- or p-hydroxyphenyl, o-, m- or p-methoxyphenyl, o-, m- or p-fluorophenyl. The radical R$^1$ is acyl, —CO—R$^5$ or else an amino protective group which is known per se; acetyl is particularly preferred.

The expression "amino protective group" is generally known and relates to groups which are suitable for protecting (for blocking) an amino group from chemical reactions, but which are easily removable after the desired chemical reaction has been carried out at other positions in the molecule. Typical groups of this type are, in particular, unsubstituted acyl, aryl, aralkoxymethyl or aralkyl groups. Since the amino protective groups are removed after the desired reaction (or reaction sequence), their nature and size is otherwise uncritical; however, those having 1–20, in particular 1–8, C atoms are preferred. The expression "acyl group" is to be interpreted in the widest sense in connection with the present process and the present compounds. It includes acyl groups derived from, aliphatic, araliphacic, aromatic or heterocyclic carboxylic acids or sulfonic acids and also, in particular, alkoxycarbonyl, aryloxycarbonyl and especially aralkoxycarbonyl groups. Examples of acyl groups of this type are alkanoyl such as acetyl, propionyl, butyryl: aralkanoyl such as phenylacetyl; aroyl such as benzoyl or toluyl; aryloxyalkanoyl such as phenoxyacetyl; alkoxycarbonyl such as methoxycarbonyl, ethoxycarbonyl, 2,2,2-trichloro-ethoxycarbonyl, BOC (tert-butoxycarbonyl), 2-iodoethoxycarbonyl; aralkyloxycarbonyl such as CBZ (carbobenzoxycarbonyl, also called 4-methoxybenzyloxycarbonyl, FMOC (9-fluorenylmethoxy-carbonyl); arylsulfonyl such as Mtr (4-methoxy-2,3,6-trimethylphenylsulfonyl). Preferred amino protective groups are BOC and Mtr, an addition CBZ or FMOC.

The compounds of the formula I can have one or more chiral centres and therefore occur in various stereoisomeric forms. The formula I includes all these forms.

The invention furthermore relates to a process for the preparation of chroman derivatives of the formula I according to claim 1 and also of their salts, in which X is O, characterized in chat a compound of the formula II

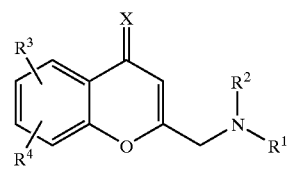

in which R$^1$, R$^2$, R$^3$, R$^4$ have the meanings indicated in claim 1 and X is O, is hydrogenated with the aid of an enantiomerically enriched catalyst.

The invention also relates to a process for the preparation of chroman derivatives of the formula I according to claim 1 and also of their salts, in which X is H,H, characterized in that a compound of the formula II

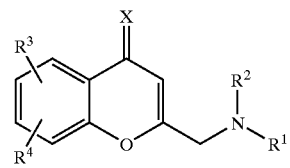

in which R$^1$, R$^2$, R$^3$, R$^4$ have the meanings indicated in claim 1 and X is O, is hydrogenated with the aid of an enantiomerically enriched catalyst, and then reduced in the customary manner.

In particular, it has been found that (2-acetylaminomethyl)chromen-4-one can be hydrogenated using various enantiomerically pure rhodium-diphosphane complexes to give enantiomerically enriched (2-acetylaminomethyl)chroman-4-one.

The invention also relates to a process for the preparation of chroman derivatives of the formula I, characterized in that the enantiomerically enriched catalyst is a transition metal complex.

Particularly preferably, the catalyst is a transition metal complex comprising a metal selected from the group rhodium, iridium, ruthenium and palladium.

The invention furthermore relates to a process for the preparation of chroman derivatives of the formula I, characterized in that the catalyst is a transition metal complex in which the transition metal is complexed with a chiral diphosphane ligand.

The ligands below may be mentioned by way of example:

(S)-EtDuphos:

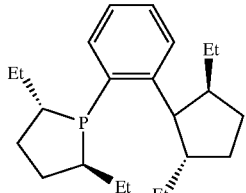

BINAP:

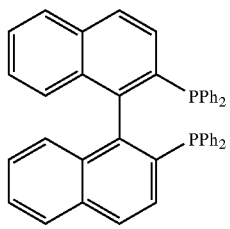

(S,S)-Chiraphos:

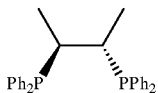

(S,S)-DIOP:

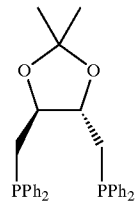

(S,S)-Skewphos (BDPP):

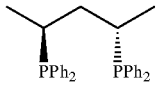

(S,S)-BPPM:

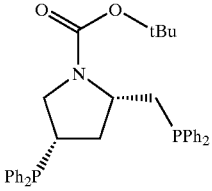

(R,R)-Norphos:

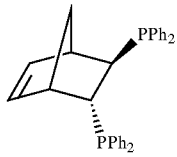

(S,R)-BPPFOH:

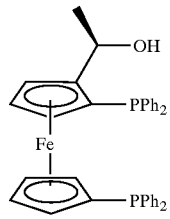

(S,R)-PFctBu:

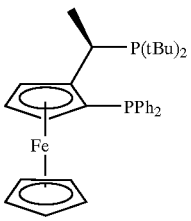

Depending on the choice of the (R) or (S) enantiomer of the ligand in The catalyst, the (R) or (S) enantiomer is obtained in an excess.

Precursors used for the chiral ligands are compounds such as, for example, $Rh(COD)_2OTf$ (rhodium-cyclooctadiene triflate), $[Rh(COD)Cl]_2$, $Rh(COD)_2BF_4$, $[Ir(COD)Cl]_2$, $Ir(COD)_2BF_4$ or $[Ru(COD)Cl_2]_x$.

The compounds of the formula I and also the starting substances for their preparation are otherwise prepared by methods known per se, such as are described in the literature (e.g. in the standard works such as Houben-Weyl, Methoden der organischen Chemie [Methods of Organic Chemistry], Georg-Thieme-Verlag, Stuttgart), mainly under reaction conditions which are known and suitable for the reactions mentioned. Use can also be made in this case of variants which are known per se, but not mentioned here in greater detail.

If desired, the starting substances can also be formed in situ such that they are not isolated from the reaction mixture, but immediately reacted further to give the compounds of the formula I.

The compounds of the formula II are known in some cases; the unknown compounds can easily be prepared analogously to the known compounds.

The conversion of a compound of the formula II in which X is O into a compound of the formula I in which X is O is carried out according to the invention using hydrogen gas with the aid of an enantiomerically enriched catalyst in an inert solvent such as, for example, methanol or ethanol.

Suitable inert solvents are furthermore, for example, hydrocarbons such as hexane, petroleum ether, benzene, toluene or xylene; chlorinated hydrocarbons such as trichloroethylene, 1,2-dichloroethane, carbon tetrachloride, chloroform or dichloromethane; alcohols such as isopropanol, n-propanol, n-butanol or tert-butanol; ethers such as diethyl ether, diisopropyl ether, tetrahydrofuran (THF) or dioxane; glycol ethers such as ethylene glycol monomethyl or monoethyl ether (methyl glycol or ethyl glycol), ethylene glycol dimethyl ether (diglyme); ketones such as acetone or butanone; amides such as acetamide, dimethylacetamide or dimethylformamide (DMF); nitrites such as acetonitrile; sulfoxides such as dimethyl sulfoxide (DMSO); carbon disulfide; nitro compounds such as nitromethane or nitrobenzene; esters such as ethyl acetate, and optionally also mixtures of the solvents mentioned with one another or mixtures with water.

The reaction time of the enantioselective hydrogenation, depending on the conditions used, is between a few minutes and 14 days; the reaction temperature is between 0 and 150°, normally between 20 and 130°.

Customarily, the catalyst/substrate ratio is between 1:2000 and 1:50, particularly preferably 1:1000 and 1:100. The reaction time is then, for example, between 3 and 20 hours. The hydrogenation is carried out under 1–200 bar of hydrogen, preferably at 3–100 bar.

The conversion of a compound of the formula II in which X is O into a compound of the formula I in which X is H,H is carried out according to the invention using hydrogen gas with the aid of an enantiomerically enriched catalyst in an inert solvent such as methanol or ethanol, such as described above, followed by a conversion of the 4-oxo group into a methylene group according to known conditions. The reduction is preferably carried out using hydrogen gas under transition metal catalysis (for example by hydrogenation on Raney nickel or Pd-carbon in an inert solvent such as methanol or ethanol).

The conversion of compounds of the formula I in which $R^3$, $R^4$ is COOalkyl into compound s of the formula I in which $R^3$, $R^4$ is COOH is carried out, for example, using NaOH or KOH in water, water-THF or water-dioxane at temperatures between 0 and 100°.

The removal of a radical $R^1$ from a compound of the formula I is carried out—depending on the protective group used—for example using strong acids, expediently using TFA (trifoluoroacetic acid) or perchloric acid, but also using other strong inorganic acids such as hydrochloric acid or sulfuric acid, strong organic carboxylic acids such as trichloroacetic acid or sulfonic acids such as benzene or p-toluenesulfonic acid. The presence of an additional inert solvent is possible, but not always necessary. Suitable inert solvents are preferably organic solvents, for example carboxylic acids such as acetic acid, ethers such as tetrahydrofuran or dioxane, amides such as dimethylformamide, halogenated hydrocarbons such as dichloromethane, in addition also alcohols such as methanol, ethanol or isopropanol and also water. In addition, mixtures of the abovementioned solvents are possible. TFA is preferably used in an excess without addition of a further solvent, perchloric acid in the form of a mixture of acetic acid and 70% perchloric acid in the ratio 9:1. The reaction temperatures are expediently between approximately 0 and approximately 50°; the reaction is preferably carried out between 15 and 30°.

The BOC group is preferably removed using TFA in dichloromethane or using approximately 3 to 5 N hydrochloric acid in dioxane at 15–30°. The removal of the acetyl group is carried out according to customary methods (P. J. Kocienski, *Protecting Groups*, Georg Thieme Verlag, Stuttgart, 1994).

Hydrogenolytically removable protective groups (e.g. CBZ or benzyl) can be removed, for example, by treating with hydrogen in the presence of a catalyst (e.g. of a noble metal catalyst such as palladium, expediently on a support such as carbon). Suitable solvents in this case are those indicated above, in particular, for example, alcohols such as methanol or ethanol or amides such as DMF. As a rule, the hydrogenolysis is carried out at temperatures between approximately 0 and 100° and pressures between approximately 1 and 200 bar, preferably at 20–30° and 1–10 bar.

A base of the formula I can be converted into the associated acid addition salt using an acid, for example by reaction of equivalent amounts of the base and of the acid in an inert solvent such as ethanol and subsequent evaporation. For this reaction, suitable acids are particularly those which yield physiologically acceptable salts. Thus inorganic acids can be used, e.g. sulfuric acid, nitric acid, hydrohalic acids such as hydrochloric acid or hydrobromic acid, phosphoric acids such as orthophosphoric acid, sulfamic acid, in addition organic acids, in particular aliphatic, alicyclic, araliphatic, aromatic or heterocyclic mono- or polybasic carboxylic, sulfonic or sulfuric acids, e.g. formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane or ethanesulfonic acid, ethanedisulfonic acid, 2-hydroxyethanesulfonic acid, benzenesulfonic acid, p-toluenesulfonic acid, naphthalenemono- and disulfonic acids and laurylsulfuric acid. Salts with physiologically unacceptable acids, e.g. picrates, can be used for the isolation and/or purification of the compounds of the formula I.

On the other hand, compounds of the formula I can be converted into the corresponding metal salts, in particular alkali metal or alkaline earth metal salts, using bases (e.g. sodium or potassium hydroxide or carbonate), or into the corresponding ammonium salts.

The invention furthermore relates to the use of the compounds of the formula I as intermediates for the synthesis of medicaments. Appropriate medicaments are described, for example, in EP 0 707 007.

The invention accordingly relates in particular to the use of the compounds of the formula I according to claim 1 in the synthesis of
(R)-2-[5-(4-fluorophenyl)-3-pyridylmethylaminomethyl]-chroman and its salts, characterized in that
a) a compound of the formula II

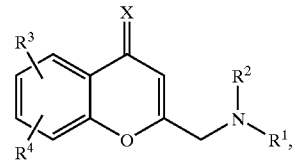

in which
$R^1$ has the meaning indicated in claim 1,
$R^2$, $R^3$ and $R^4$ are H and X is O,
is hydrogenated with the aid of an enantiomerically enriched catalyst,
b) in that, from the enantiomerically enriched mixture of the (R) and (S) compounds of the formula I thus obtained, in which
$R^1$ has the meaning indicated in claim 1,
$R^2$, $R^3$ and $R^4$ are H and X is O.
the enantiomerically pure (R) compound of the formula I, in which
$R^1$ has the meaning indicated in claim 1,
$R^2$, $R^3$ and $R^4$ are H and X is O,
is obtained by crystallization, in that
c) the enantiomerically pure (R) compound of the formula I, in which
$R^1$ has the meaning indicated in claim 1,
$R^2$, $R^3$ and $R^4$ are H and X is O,
is then reduced in the customary manner, in that
d) the radical $R^1$ in which
$R^1$ has the meaning indicated in claim 1,
$R^2$, $R^3$ and $R^4$ are H and X is H,H,
is removed from the (R) compound of the formula I thus obtained, in that
e) the (R)-(chroman-2-ylmethyl)amine thus obtained is converted into its acid addition salt and this is reacted in a known manner to give (R)-2-[5-(4-fluorophenyl)-3-pyridylmethylaminomethyl]chroman and, if appropriate, converted into its acid addition salt, where the recovery of the (R) enantiomer can also be carried out by crystallization from the enantiomerically enriched (R,S) mixture after stage c) or after stage d).

The invention furthermore relates to the use of the compounds of the formula I as intermediates for the synthesis of medicaments which show actions on the central nervous system.

Above and below, all temperatures are indicated in °C. In the following examples, "customary working up" means: if necessary, water is added, the mixture is adjusted, if necessary, depending on the constitution of the final product, to a pH of between 2 and 10 and extracted with ethyl acetate or dichloromethane, the organic phase is separated off, dried over sodium sulfate and evaporated, and the residue is purified by chromatography on silica gel and/or by crystallization. $R_f$ values on silica gel.

EXAMPLE

Experimental data (complex preparation, hydrogenation, analytical methods):

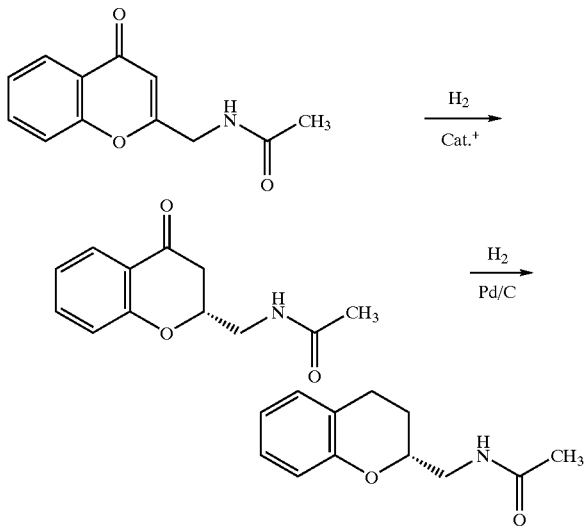

All reactions were carried out under inert conditions (i.e. anhydrous and oxygen-free reaction conditions).

1. Preparation of the Catalyst/Substrate Solution 1.1. Example 11.2 mg of $Rh(COD)_2OTf$ (rhodium-cyclooctadiene triflate) were dissolved in 5 ml of methanol and cooled to 0° C. A cooled solution of 1.1 eq of bisphosphane (e.g. 12.6 mg of (R,R)-Skewphos) in 5 ml of methanol was then added. After stirring at room temperature for 10 min, the complex solution was treated with the substrate solution consisting of 110 mg of (2-acetylaminomethyl)chromen-4-one in 10 ml of methanol.

1.2. Example 51.4 mg of $[Rh(COD)Cl]_2$ were dissolved in 4 ml of the solvent mixture toluene/methanol 5:1 and treated with a solution consisting of 5 ml of toluene, 1 ml of methanol and 1.1 eq of bisphosphane (e.g. 130.6 mg of (R)-BINAP). 1 ml of this catalyst complex solution was added to 510.8 mg of (2-acetylaminomethyl)chromen-4-one, dissolved in 15 ml of toluene and 3 ml of methanol.

2. Enantioselective Hydrogenation

The catalyst/substrate solution to be hydrogenated was filled into an autoclave in a countercurrent of protective gas. The protective gas atmosphere was replaced by flushing several times with hydrogen (1–5 bar $H_2$ atmosphere). The batches analogous to 1.1. reacted even at room temperature and 5 bar of hydrogen. The catalysts analogous to 1.2. afforded the best results at 50° C. and 80 bar of hydrogen. As a rule, the hydrogenation was terminated after 15 hours.

3. Sampling and Analytical Methods

A sample was taken in a countercurrent of protective gas. The complex was separated off by column chromatography on silica gel (eluent: ethyl acetate) before the determination of the enantiomeric excesses.

The enantiomeric excess of the hydrogenation product was determined on the chiral HPLC phase:

| | |
|---|---|
| Column: | Daicel Chiralcel OJ (I.D. × length/mm: 4.6 × 250) |
| Eluent: | n-hexane: i-propanol = 9:1 |
| Flow: | 0.8 ml/min (18 bar, 28° C.) |
| Detection: | UV 250 nm |
| Retention: | $R_t$ (R) = 27 min; $R_t$ (S) = 29 min |

The concentration of the crude hydrogenation solution led to the precipitation of the product. An increase in the enantiomeric excess was detected by means of fractional crystallization.

4. Further Reduction

After complete conversion was detected, the reduction of the keto group was carried out by means of palladium-carbon as a one-pot process. The crude ketone solution resulting from the homogeneous hydrogenation was treated with 10% by weight water-moist palladium-carbon (e.g. 100 mg of water-moist Pd/C to 1 g of (2-acetylaminomethyl) chromen-4-one) and 1 ml of glacial acetic acid. Hydrogenation was carried out at a hydrogen pressure of 7 bar and 50° C. for 14 h.

5. Work-up and Analytical Methods

The palladium-carbon was removed by filtration. The enantiomeric excess of the hydrogenation product was determined on a chiral HPLC phase:

| | |
|---|---|
| Column: | Daicel Chiralcel OJ (I.D. × length/mm: 4.6 × 250) |
| Eluent: | n-hexane: i-propanol = 9:1 |
| Flow: | 0.8 ml/min (18 bar, 28° C.) |
| Detection: | UV 250 nm |
| Retention: | $R_t$ (R) = 25 min; $R_t$ (S) = 27 min |

During the reduction with palladium-carbon, the enantiomeric excess remained unchanged.

The concentration of the crude hydrogenation solution led to the precipitation of the product. An increase in the enantiomeric excess was detected by means of fractional crystallization.

Enantioselectivities of the Homogeneous Hydrogenation

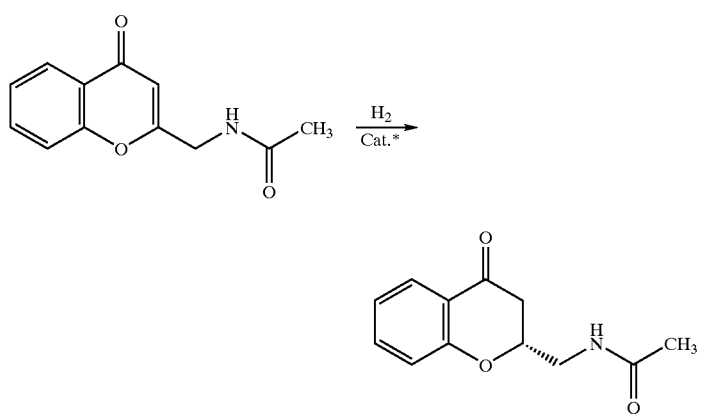

| Elab No. | Complex:metal anion ligand (addition) | Solvent | Pressure | % ee |
|---|---|---|---|---|
| 1. | 18 | Rh—OTf-(R,R)-EtDuphos | CH$_2$Cl$_2$ | 1 | 55 S |
| 2. | 13 | Rh—OTf-(R,R)-EtDuphos | THF | 1 | 44 S |
| 3. | 14 | Rh—OTf-(R,R)-EtDuphos | MeOH | 1 | 64 S |
| 4. | 15 | Rh—OTf-(R,R)-EtDuphos | EE | 1 | 33 S |
| 5. | 6 | Rh—OTf-(R,R)-EtDuphos | iPrOH | 1 | 20 S |
| 6. | 23a | Rh—OTf-(R,R)-EtDuphos | MeOH | 1 | 34 S |
| 7. | 23b | Rh—OTf-(R,R)-EtDuphos | MeOH | 1 | 36 S |
| 8. | 23c | Rh—OTf-(R,R)-EtDuphos | MeOH | 5 | 45 S |
| 9. | 23d | Rh—OTf-(R,R)-EtDuphos | MeOH | 5 | 31 S |
| 10. | 12 | Ru—Cl$_2$-(R)-BINAP (AgOOCCF$_3$) | iPrOH | 5 | 50 S |
| 11. | 19 | Rh—ClO$_4$-(S,S)-Chiraphos | iPrOH | 1 | — |
| 12. | 20 | Rh—OTf-(S,S)-DIOP | THF | 1 | rac. |
| 13. | 20 | Rh—OTf-(S,S)-DIOP | THF | 3 | 8 R |
| 14. | 21 | Rh—OTf(R,R)-Skewphos | THF | 1 | — |
| 15. | 22b | Rh—OTf-(S,S)-BPPM | MeOH | 1 | 7 S |
| 16. | 24a | Rh—OTf-(R,S)-BPPFOH | MeOH | 1 | 54 R |
| 17. | 24b | Rh—OTf-(R,S)-BPPPOH | MeOH | 1 | 54 R |
| 18. | 24c | Rh—OTf-(R,S)-BPPFOH | MeOH | 5 | 63 R |
| 19. | 25a | Rh—OTf-(R)-BINAP | MeOH | 1 | 1 R |
| 20. | 25b | Rh—OTf-(R)-BINAP | MeOH | 5 | rac. |
| 21. | 26a | Rh—OTf-(S,S)-Norphos | MeOH | 1 | 42 R |
| 22. | 26b | Rh—OTf-(S,S)-Norphos | MeOH | 5 | 60 R |
| 23. | 26c | Rh—OTf-(S,S)-Norphos | iPrOH | 5 | 12 R |
| 24. | 26d | Rh—OTf-(S,S)-Norphos | THF | 5 | 3 R |
| 25. | 27a | Rh—OTf-(S,S)-Norphos | MeOH | 8 | 64 R |
| 26. | 27b | Rh—Cl-(S,S)-Norphos | MeOH | 8 | 40 R |
| 27. | 27c | Rh—OTf-(S,S)-Norphos | MeOH | 30 | 65 R |
| 28. | 27d | Rh—OTf-(S,S)-Norphos | MeOH | 60 | 64 R |
| 29. | 28a | Rh—OTf-(R,R)-EtDUPhos | MeOH | 10 | 16 S |
| 30. | 28b | Rh—OTf-(R,R)-EtDUPhos | MeOH | 30 | 28 S |
| 31. | 29a | Rh—OTf-(R,R)-BPPFOH | MeOH | 10 | 55 R |
| 32. | 29b | Rh—OTf-(R,S)-BPPFOH | MeOH | 30 | 56 R |
| 33. | 37 | Rh—ClO$_4$-(S,S)-Chiraphos | MeOH | 10 | 30 R |
| 34. | 38 | Rh—OTf-(S,S)-DIOP | MeOH | 10 | rac. |
| 35. | 39 | Rh—OTf-(R,R)-Skewphos | MeOH | 10 | 46 S |
| 36. | 40 | Rh—OTf-(S,S)-BPPM | MeOH | 10 | 9 S |
| 37. | 41 | Ir—Cl-(S,S)-DIOP | MeOH | 10 | 8 R |
| 38. | 42 | Ir—Cl-(S,S)-DIOP | CH$_2$Cl$_2$ | 10 | 7 S |
| 0. | 43 | Ir—Cl-(S,S)-DIOP (+I) | MeOH | 10 | — |
| 1. | 44 | Ir—Cl-(S,S)-DIOP (+I) | MeOH | 30 | — |
| 2. | 45 | Ir—Cl-(S,S)-DIOP (+I + CH$_3$COOH) | MeOH | 10 | — |
| 3. | 46 | Ir—OTf-(S,S)-DIOP | MeOH | 10 | 11 R |
| 4. | 47 | Ir—OTf-(S,S)-DIOP (+I) | MeOH | 10 | 39 R |
| 5. | 49 | Rh—OTf-(S,S)-Norphos | MeOH | 10, RT | 57 R |
| 6. | 50 | Rh—OTf-(S,S)-Norphos | MeOH | 10, 50° C. | 60 R |
| 7. | 52 | Rh—BF$_4$-(R,S)-PFctB | MeOH | 10, 50° C. | 33 S |
| 8. | 54 | Rh—Cl-(R)-BINAP | Tol:MeOH 5:1 | 80, 50° C. | 91 S |
| 9. | 59 | Rh—Cl-(S,S)-Norphos | Tol:MeOH 5:1 | 80, 50° C. | 19 R |
| 10. | 62 | crude 59/Pd/C | Tol:MeOH 5:1 | 7, 50° C. | 18 R |

What is claimed is:

1. A chroman compound of formula I

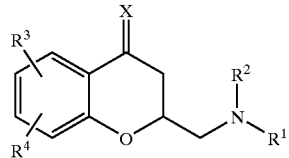

in which

R¹ is acyl having 1–6 C atoms, —CO—R⁵ or an amino protective group,

R² is H or alkyl having 1–6 C atoms,

R³, R⁴ in each case independently of one another are H, alkyl having 1–6 C atoms, CN, Hal or COOR², R⁵ is phenyl which is unsubstituted or mono- or disubstituted by alkyl having 1–6 C atoms, OR² or Hal, X is H, H or O, Hal is F, Cl, Br or I, or a physiologically acceptable salt thereof, wherein said compound is not N-(Chroman-2-ylmethyl)-cyclopropane carboxylic acid amide.

2. An enantiomer of the compound of claim 1.

3. The compound according to claim 1, wherein said compound is a) N-(4-oxochroman-2-ylmethyl)acetamide;

b) N-(chroman-2-ylmethyl)acetamide;

c) (S)-N-(4-oxochroman-2-ylmethyl)acetamide;

d) (R)-N-(4-oxochroman-2-ylmethyl)acetamide;

e) (S)-N-(chroman-2-ylmethyl)acetamide; or f) (R)-N-(chroman-2-ylmethyl)acetamide.

4. A process for the preparation of a compound according to claim 1 in which X is O, wherein a compound of formula II

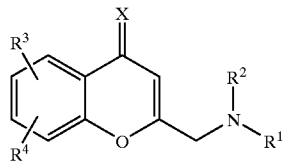

in which

R¹ is acyl having 1–6 C atoms, —CO—R⁵ or an amino protective group,

R² is H or alkyl having 1–6 C atoms,

R³, R⁴ in each case independently of one another are H, alkyl having 1–6 C atoms, CN, Hal or COOR², and X is O, is hydrogenated with a chiral catalyst.

5. A process for the preparation of the compound according to claim 1 in which X is H, H, wherein a compound of formula II

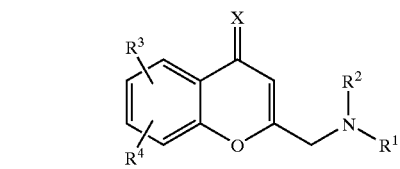

in which

R¹ is acyl having 1–6 C atoms, —CO—R⁵ or an amino protective group,

R² is H or alkyl having 1–6 C atoms,

R³, R⁴ in each case independently of one another are H, alkyl having 1–6 C atoms, CN, Hal or COOR², and X is O, is hydrogenated with a chiral catalyst, and reduced.

6. The process according to claim 4, wherein the catalyst is a transition metal complex.

7. The process according to claim 4, wherein the catalyst is a transition metal complex comprising rhodium, iridium, ruthenium or palladium.

8. The process according to claim 4, wherein the catalyst is a transition metal complex in which the a transition metal is complexed with a chiral diphosphane ligand.

9. A method for the synthesis of (R)-2-[5-(4-fluorophenyl)-3-pyridylmethylaminomethyl]chroman, or a salt thereof, comprising:

a) hydrogenating with a chiral catalyst, a compound of the formula II

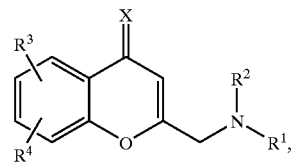

in which

R¹ is acyl having 1–6 C atoms, —CO—R⁵ or an amino protective group,

R², R³ and R⁴ are H and X is O;

b) crystalizing the enantiomeric (R) compound from the enantiomerically enriched mixture of (R) and (S) compounds thus obtained;

c) reducing the enantiomeric (R) compound from b);

d) removing the R¹ radical from the (R) compound thus obtained to produce (R)-(chroman-2-ylmethyl)amine; and e) converting the (R)-(chroman-2-ylmethyl)amine to its an acid addition salt and reacting said acid addition salt to give (R)-2-[5-(4-fluorophenyl)-3-pyridylmethylaminomethyl]chroman.

10. The method of claim 9, wherein (R)-2-[5-(4-fluorophenyl)-3-pyridylmethylaminomethyl]chroman is converted to an acid addition salt.

11. A method for the synthesis of (R)-2-[5-(4-fluorophenyl)-3-pyridylmethylaminomethyl]chroman, or a salt thereof, comprising:

a) hydrogenating with a chiral catalyst, a compound of the formula II

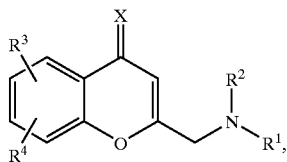

in which
R¹ is acyl having 1–6 C atoms, —CO—R⁵ or an amino protective group,
R², R³ and R⁴ are H and X is O;
b) reducing the enantiomerically enriched mixture of (R) and (S) compounds thus obtained;
c) crystalizing the enantiomeric (R) compound from the enantiomerically enriched mixture of (R) and (S) compounds;
d) removing the R¹ radical from the (R) compound thus obtained to produce (R)-(chroman-2-ylmethyl)amine; and
e) converting the (R)-(chroman-2-ylmethyl)amine to an acid addition salt and reacting said acid addition salt to give (R)-2-[5-(4-fluorophenyl)-3-pyridylmethylaminomethyl]chroman.

12. The method of claim 11, wherein (R)-2-[5-(4-fluorophenyl)-3-pyridylmethylaminomethyl]chroman is converted to an acid addition salt.

13. A method for the synthesis of (R)-2-[5-(4-fluorophenyl)-3-pyridylmethylaminomethyl]chroman, or a salt thereof, comprising:
a) hydrogenating with a chrial catalyst, a compound of the formula II

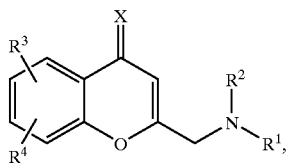

in which
R¹ is acyl having 1–6 C atoms, —CO—R⁵ or an amino protective group,
R², R³ and R⁴ are H and X is O;
b) reducing the enantiomerically enriched mixture of (R) and (S) compounds thus obtained;
c) removing the R¹ radical from the compounds thus obtained;
d) crystalizing the enantiomeric (R) compound from the enantiomerically enriched mixture of (R) and (S) compounds; and
e) converting the enantiomeric (R) compound to an acid addition salt and reacting said acid addition salt to give (R)-2-[5-(4-fluorophenyl)-3-pyridylmethylaminomethyl]chroman.

14. The method of claim 13, wherein (R)-2-[5-(4-fluorophenyl)-3-pyridylmethylaminomethyl]chroman is converted to an acid addition salt.

15. A pharmaceutical composition comprising a compound of claim 1.

16. The compound of claim 1, wherein R¹ is acyl with 1–6 C atoms or —CO—R⁵.

17. The process according to claim 5, wherein the catalyst is a transition metal complex.

18. The process according to claim 5, wherein the catalyst is a transition metal complex comprising rhodium, iridium, ruthenium or palladium.

19. The process according to claim 5, wherein the catalyst is a transition metal complex in which the transition metal is complexed with a chiral diphosphane ligand.

20. The process according to claim 9, wherein the catalyst is a transition metal complex.

21. The process according to claim 9, wherein the catalyst is a transition metal complex comprising rhodium, iridium, ruthenium or palladium.

22. The process according to claim 9, wherein the catalyst is a transition metal complex in which the transition metal is complexed with a chiral diphosphane ligand.

23. The process according to claim 11, wherein the catalyst is a transition metal complex.

24. The process according to claim 11, wherein the catalyst is a transition metal complex comprising rhodium, iridium, ruthenium or palladium.

25. The process according to claim 11, wherein the catalyst is a transition metal complex in which the transition metal is complexed with a chiral diphosphane ligand.

26. The process according to claim 13, wherein the catalyst is a transition metal complex.

27. The process according to claim 13, wherein the catalyst is a transition metal complex comprising rhodium, iridium, ruthenium or palladium.

28. The process according to claim 13, wherein the catalyst is a transition metal complex in which the transition metal is complexed with a chiral diphosphane ligand.

* * * * *

UNITED STATES PATENT AND TRADEMARK OFFICE
CERTIFICATE OF CORRECTION

PATENT NO. : 6,646,136 B1 Page 1 of 1
DATED : November 11, 2003
INVENTOR(S) : Heinz-Herman Bokel et al.

It is certified that error appears in the above-identified patent and that said Letters Patent is hereby corrected as shown below:

Title page,
Item [75], Inventors, line 3, "Müramann," should read -- Mürmann --

Column 12,
Line 27, reads "which the a," should read -- which a --
Line 56, reads "to its," should read -- to --

Signed and Sealed this

Seventh Day of September, 2004

JON W. DUDAS
*Director of the United States Patent and Trademark Office*